(12) United States Patent
Wang

(10) Patent No.: US 10,314,931 B2
(45) Date of Patent: Jun. 11, 2019

(54) AIR SCAVENGER COMPOSITION

(71) Applicant: Jingning Wang, Huizhou (CN)

(72) Inventor: Jingning Wang, Huizhou (CN)

( * ) Notice: Subject to any disclaimer, the term of this patent is extended or adjusted under 35 U.S.C. 154(b) by 0 days.

(21) Appl. No.: 16/069,855

(22) PCT Filed: May 26, 2017

(86) PCT No.: PCT/CN2017/086140
§ 371 (c)(1),
(2) Date: Jul. 12, 2018

(87) PCT Pub. No.: WO2018/028274
PCT Pub. Date: Feb. 15, 2018

(65) Prior Publication Data
US 2019/0030200 A1    Jan. 31, 2019

(30) Foreign Application Priority Data
Aug. 10, 2016 (CN) .......................... 2016 1 0652424

(51) Int. Cl.
*A61L 9/013* (2006.01)
*A61L 9/01* (2006.01)

(52) U.S. Cl.
CPC ................. *A61L 9/013* (2013.01); *A61L 9/01* (2013.01); *A61L 2209/21* (2013.01)

(58) Field of Classification Search
None
See application file for complete search history.

(56) References Cited

FOREIGN PATENT DOCUMENTS

| | | |
|---|---|---|
| CN | 1453276 A | 11/2003 |
| CN | 101920029 A | 12/2010 |
| CN | 103505748 A | 1/2014 |
| CN | 104474170 A | 4/2015 |
| CN | 106075521 A | 8/2017 |
| EP | 1439147 A1 | 10/2003 |

*Primary Examiner* — Susan Hoffman
(74) *Attorney, Agent, or Firm* — Culhane Meadows PLLC; Robert C. Klinger

(57) ABSTRACT

The present invention provides an air scavenger composition comprising by weight at least: extracts of *sanguisorba officinalis* and *melia azadarach* 10-30 parts, extract of *sophora flavescens* 10-30 parts, extract of *robinia pseudoacacia* 5-10 parts, extract of *eucalyptus* leaves 1-5 parts, extract of *chrysanthemum* 10-15 parts, extract of *aloe vera* 10-15 parts, nanosilver 0.1-1 parts, and artemisinin 0.5-2 parts.

8 Claims, No Drawings

AIR SCAVENGER COMPOSITION

FIELD OF THE INVENTION

The present invention relates to the field of environment health, and particularly relates to an air scavenger composition.

DESCRIPTION OF THE PRIOR ART

With the gradual improvement of people's living standard, contrarily, the quality of the air environment decreases gradually, so requirements of people on air purification are getting higher and higher. Now there are many air scavengers on the market, generally speaking there are several types as follow: adsorption type air scavenger, covering type odor removing product, and decomposition type odor removing product.

The adsorption type air scavenger removes the contaminants in air by using the properties such as physical adsorption, chemical adsorption, oxidation, catalytic oxidation and reduction of the materials similar to activated carbon. The covering type air scavenger covers odor of a substance by using a volatile substance having a fragrance, creating an illusion of air purification to people. The decomposition type air scavenger is a material similar to $TiO_2$ in the scavenger, it can produce hydroxyl radical and superoxide radical from oxygen gas or water molecule under sunlight, the hydroxyl radical and superoxide radical have very strong oxidization and reduction capability, so as to cause oxidative decomposition of harmful substances in air. Most of the existing air scavengers are made by mixing of organic compounds such as aromatics and some monoterpenoids, and then adding an amount of essence, which have certain toxic and side effects and are unsafe.

SUMMARY OF THE INVENTION

In order to solve the problem in prior art, a first aspect of the present invention provides an air scavenger composition, it comprises by weight at least:

| | |
|---|---|
| extract of *sanguisorba officinalis* and *melia azadarach* | 10-30 parts |
| extract of *sophora flavescens* | 10-30 parts |
| extract of *robinia pseudoacacia* | 5-10 parts |
| extract of *eucalyptus* leaves | 1-5 parts |
| extract of *chrysanthemum* | 10-15 parts |
| extract of *aloe vera* | 10-15 parts |
| nanosilver | 0.1-1 parts |
| artemisinin | 0.5-2 parts. |

In some embodiments, said air scavenger composition comprises by weight at least:

| | |
|---|---|
| extract of *sanguisorba officinalis* and *melia azadarach* | 15-25 parts |
| extract of *sophora flavescens* | 15-25 parts |
| extract of *robinia pseudoacacia* | 7-8 parts |
| extract of *eucalyptus* leaves | 2-4 parts |
| extract of *chrysanthemum* | 12-14 parts |
| extract of *aloe vera* | 11-13 parts |
| nanosilver | 0.4-0.6 part |
| artemisinin | 0.8-1.2 parts. |

In some embodiments, said air scavenger composition comprises by weight at least:

| | |
|---|---|
| extract of *sanguisorba officinalis* and *melia azadarach* | 20 parts |
| extract of *sophora flavescens* | 20 parts |
| extract of *robinia pseudoacacia* | 8 parts |
| extract of *eucalyptus* leaves | 3 parts |
| extract of *chrysanthemum* | 13 parts |
| extract of *aloe vera* | 12 parts |
| nanosilver | 0.5 part |
| artemisinin | 1 part. |

In some embodiments, an extraction method of said extract of *sanguisorba officinalis* and *melia azadarach* is: *sanguisorba officinalis* and *melia azadarach* are respectively washed, and chopped, then *sanguisorba officinalis* and *melia azadarach* are uniformly mixed, extracted under reflux with ethanol for 2-3 hours, extracted 3-4 times, refrigerated for 10-15 hours, and filtered, the filtrate is concentrated under a reduced pressure until no ethanol is present, to obtain the extract.

In some embodiments, the weight ratio of said *sanguisorba officinalis* to said *melia azadarach* is 1:(2.5-3.5).

In some embodiments, an extraction method of the extract of said *sophora flavescens* is: *sophora flavescens* is washed, and chopped, then added into a citric acid aqueous solution, immersed for 2-3 hours, then heated by microwave and extracted 2-3 times, and filtered, the filtrate is dried under a reduced pressure, to obtain the extract.

In some embodiments, a mass concentration of said citric acid aqueous solution is 2-5 g/L.

In some embodiments, a weight ratio of said *sophora flavescens* to the citric acid aqueous solution is 1:(9-11).

In some embodiments, particle diameter of said nanosilver is 1-20 nm.

A second aspect of the present invention provides an air scavenger, including the above-mentioned air scavenger composition.

The air scavenger composition provided by the present invention is prepared by using plant raw materials, it is safe and harmless, and has a good stability and a long effective time.

DETAILED DESCRIPTION OF THE PREFERRED EMBODIMENTS

The content of the present invention can be understood more easily by reference to the following detailed description of the preferred embodiments of the present invention and the included examples. Unless otherwise specified, all technical and scientific terms used herein have same meaning as generally understood by one skilled in the field of the present invention. In case of contradiction, the definition in this specification shall prevail.

The term "prepared from" used herein has the same meaning as "include". The terms "include", "comprise", "have", "contain" or its any other variants are intended to cover non-exclusive "comprise". For example, a composition, a step, a method, a product or a device including the listed elements are not necessary to be limited to those elements, but it may comprise other elements unlisted or inherent elements of such a composition, step, method, product or device.

The phrase "consist of" excludes any element, step or component not indicated. If being used in the claims, this phrase will make the claims to be in a closed fashion, and make it not include material other than the described material, except the conventional impurities related to it. When the phrase "consist of" occurs in a clause of a claim rather than immediately follows the preamble, it only defines the element(s) described in the clause; other elements are not excluded from said claim as a whole.

When an equivalent, concentration, or other value or parameter is represented with a range, a preferred range, or a range defined by a series of preferred upper limit values and preferred lower limit values, this should be understood as specifically disclosing all range defined by any pair of an upper limit of any range or a preferred value and a lower limit of any range or a preferred value, regardless this range is specifically disclosed or not. For example, when a range of "1 to 5" is disclosed, the described range should be interpreted as comprising a range of "1 to 4", "1 to 3", "1 to 2", "1 to 2 and 4 to 5", "1 to 3 and 5", etc. When a numerical range is described herein, this range is intended to comprise its endpoint values and all integers and fractions within that range, unless otherwise specified.

The singular form comprises plural referents, unless otherwise clearly indicated in the context. "optional" or "any one" means that an item or event described thereafter may occur or not occur, and this description comprises a situation in which an event occurs and a situation in which an event does not occur.

Approximate expressions used to modify a number in the specification and the claims means that the present invention is not limited to the specific number, it also includes a modified part which is close to that number and is acceptable without causing a change of related basic function. Correspondingly, when a numerical value is modified by "approximate" and "about" etc., it means that the present invention is not limited to that exact value. In certain examples, the approximate expressions may correspond to a precision of an instrument which measures a value. In the specification and the claims of the present application, range definitions can be combined and/or exchanged, these ranges comprise all sub-ranges included therein, unless otherwise specified.

In addition, an indefinite article "a" and "an" in front of an element or component in the present invention imposes no restriction on the number of the element or component (i.e., occurring number). Thus, "a" or "an" should be interpreted as comprising one or at least one, and an element or component in singular form also includes plural form, unless the described number evidently refers to the singular form.

A first aspect of the present invention provides an air scavenger composition, comprising by weight at least:

| | |
|---|---|
| extract of *sanguisorba officinalis* and *melia azadarach* | 10-30 parts |
| extract of *sophora flavescens* | 10-30 parts |
| extract of *robinia pseudoacacia* | 5-10 parts |
| extract of *eucalyptus* leaves | 1-5 parts |
| extract of *chrysanthemum* | 10-15 parts |
| extract of *aloe vera* | 10-15 parts |
| nanosilver | 0.1-1 parts |
| artemisinin | 0.5-2 parts. |

In some embodiments, said air scavenger composition comprises by weight at least:

| | |
|---|---|
| extract of *sanguisorba officinalis* and *melia azadarach* | 15-25 parts |
| extract of *sophora flavescens* | 15-25 parts |
| extract of *robinia pseudoacacia* | 7-8 parts |
| extract of *eucalyptus* leaves | 2-4 parts |
| extract of *chrysanthemum* | 12-14 parts |

-continued

| | |
|---|---|
| extract of *aloe vera* | 11-13 parts |
| nanosilver | 0.4-0.6 part |
| artemisinin | 0.8-1.2 parts. |

In some embodiments, said air scavenger composition comprises by weight at least:

| | |
|---|---|
| extract of *sanguisorba officinalis* and *melia azadarach* | 20 parts |
| extract of *sophora flavescens* | 20 parts |
| extract of *robinia pseudoacacia* | 8 parts |
| extract of *eucalyptus* leaves | 3 parts |
| extract of *chrysanthemum* | 13 parts |
| extract of *aloe vera* | 12 parts |
| nanosilver | 0.5 part |
| artemisinin | 1 part. |

Extract of *sanguisorba officinalis* and *melia azadarach*

*Sanguisorba officinalis* is dry root of *sanguisorba officinalis* or *sanguisorba officinalis* var. *longifolia* of rosaceae plant. It is of irregular spindle or cylindrical shape, slightly curved or twisted, its length is 5-25 cm, and its diameter is 0.5-2 cm. Its surface is taupe, brown or dark purple, and it is coarse, it has longitudinal wrinkles, transverse cracks and branching root scars. *Sanguisorba officinalis* is hard, its cross-section is flat or has numerous yellowish-white to yellowish-brown incessant fibers in the cortex, its xylem is yellow or yellowish-brown, slightly in a radial arrangement. Its slice is of irregular circular or elliptical shape, has a thickness of 0.2-0.5 cm; the cross-section of the slice is purplish red or brown. The slice is odorless, and is slightly bitter.

The nature and taste of *sanguisorba officinalis* are: bitter, acid, astringent, slight cold. The efficacy of *sanguisorba officinalis* is cooling blood for hemostasis, detoxication and close sores. Its chemical components are mainly:

(sanguiin) H-1, H-2, H-3, H-4, H-5, H-6, H-7, H-8, H-9, H-10, H-11, 1,2,6-trigalloyl-β-D-glucose, 1,2,3,6-tetragalloyl-β-D-glucose, 2,3,4,6-tetragalloyl-D-glucose, 1,2,3,4,6-pentagalloyl-β-D-glucose, methyl-6-O-galloyl-β-D-glucopyranoside, methyl-6-O-digalloyl-β-D-glucopyranoside, methyl-4,6-di-O-galloyl-β-D-glucopyranoside, methyl-2,3,6-tri-O-galloyl-β-D-glucopyranoside, methyl-3,4,6-tri-O-galloyl-β-D-glucopyranoside, methyl-2,3,4,6-tetra-O-galloyl-β-D-glucopyranoside, gallic acid-3-O-β-D-(6'-O-galloyl)-glucopyranoside, 3,4,3'-tri-O-methylellagic acid, sanguisorbic acid dilactone; two kinds of galloy hamamelose derivatives: 5,2'-di-O-galloylhamamelose, 2',3,5-tri-O-galloyl-D-hamamelofuranose. The root also contains a plurality of flavan-3-ol derivatives: d-catechin, 7-O-galloyd-catechin (7-O-galloyl-(+)-catechin), 3-O-galloylprocyanidin B-3, 3-O-galloyl-procyanidin C-2, gambiriin A-1, gambiriin B-3; and zigu-glucoside I and II, sanguisorbin A, B, C, D, E (wherein, the structures of B and E have been identified), sauvissimoside R1, pomolic acid-28-O-β-D-glucopyranoside, 2,4-dihydroxy-6-methoxyacetophenone, 3,3',4-tri-O-methyl ellagic acid, 3,4,4'-tri-O-methyl ellagic acid, sanguisorbigenin, β-Sitostrol-β-D-glucoside, 3-oxo-19a-hydroxyurs-12-en-28-oic acid, 3,11-dioxo-19a-hydroxyurs-12-en-28-oic acid, pomolic acid, 2a-hydroxypomolic acid (i.e., tormentic acid).

*Melia azadarach* is flowers of *Melia azedarach* L. and *M. toosendan* Sieb.Et Zucc., it is cold in property, and bitter in taste. It has efficacy of eliminating heat and wetness, killing parasites and relieving itching. *Melia azadarach* has many components, such as: octane, 2,6-dimethylheptane, 2,5-dimethylheptane, 2-methylpropylcyclopentane, 2-methyloctane, hexanal, 3-methyloctane, 2,2,4-trimethylheptane, 2,2,6-trimethylheptane, 3,3-dimethyloctane, 2,3,6-trimethylheptane, 2,2,2,6-tetramethylheptane, 2,2,4,6,6-pentaethylheptane, 2,5,6-trimethyloctane, 2,2,7-trimethylnonane, 2,2,6-trimethyloctane, 1,2,3-trimethylbenzene, 2,6-dimethyloctane, 2,2,11,11-tetramethyldodecane, 3,7-dimethylnonane, 2,6-dimethylundecane, 2,2,4-trimethyldecane, 3,6-dimethylundecane, 2,7-dimethylundecane, 2,9-dimethylundecane, 2,2,3-trimethylnonane, 2,8-dimethylundecane, 2,8,8-trimethylundecane, nonylaldehyde, tetradecane, 2,2,8-trimethylundecane, cycloundecane, 1,4-dimethoxybenzene, decanalaldehyde, cetane, caryophyllene, 1S,2S,5R-1,4,4-trimethyltrocycle, dodecene, pentadecane, 3,7,11-trimethyl-1,6,10-dodecatriene-3-ol, nerolidol, ledol, (3,7,11-trimethyl-1,6,10-)dodecatriene-ol acetate, 6,10,14-trimethyl-2-pentadecanone, 2-methyloctadecane, diisobutyl o-dibenzoate, nonadecane, 2,6,10-trimethyltetradecane, hexadecanoic acid, 2-methyl eicosane, 3,7,11,15-tetramethyl-2-hexadecane-ol, eicosane, butyl hexadecyl carbonate, 3,7,11,15-tetramethyl-2-hexadecenol, spathulenol, heneicosane, tetracosane, pentacosane, isobutyl palmitate, cyclohexyl hexadecanoate, 2,21-dimethyldocosane, bis(2-ethylhexyl) adipate, 9-butyldocosane, octacosane.

In some embodiments, the extraction method of extract of said *sanguisorba officinalis* and *melia azadarach* is: *sanguisorba officinalis* and *melia azadarach* are respectively washed, chopped, then *sanguisorba officinalis* and *melia azadarach* are uniformly mixed, extracted under reflux with ethanol for 2-3 hours, extracted 3-4 times, refrigerated for 10-15 hours, and filtered, the filtrate is concentrated under a reduced pressure until no ethanol is present, to obtain the extract.

In some embodiments, the weight ratio of said *sanguisorba officinalis* to said *melia azadarach* is 1:(2.5-3.5).

In the process of completion of the present invention, the inventors surprisingly found that extracting with ethanol after mixing extract of said *sanguisorba officinalis* and *Melia azadarach* can significantly improve air purification effect of the composition, whereas mixing the ethanol extract of *sanguisorba officinalis* and *melia azadarach* or extracting with water after mixing extract of said *sanguisorba officinalis* and *Melia azadarach* has no this effect. The inventors deduced that the reason is that the extraction method of the present invention facilitates the dissolution of the active components.

Extract of *Sophora flavescens*

*Sophora flavescens* is dry root of *sophora flavescens*, a leguminous plant. It is cold in property and bitter in taste, and it has efficacy of clearing heat and dampness, killing insects and diuretic function. The main components in *sophora flavescens* are matrine, oxymatrine, N-oxysophocarpine, sophoridine, d-allomatrine), l-somatrine, d-sophoranol, sophoranol N-oxide, l-sophocarpine, l-sophoramine), d-N-methylcytisine, l-anagyrine, baptifoline. The root also has a plurality of flavonoids: kushenols A, B, C, D, E, F, G, H, I, J, K, L, M, N, O, kuraridin, kuraridinol, kurarinol, neokurarinol, norkurarinol, isokurarinone, for-mononetin, kurarinone, norkurarinone, methylkushenol C, l-maackiain, trifolirhizin and rtifolirhizin-6"-O-malonate, kushenin, isoanhy-droicaritin, noranhydroicaritin, xan-thohumol, isoxanthohumol, luteolin-7-glucoside. In addition, the root also has triterpenoid saponins: *sophora* flavosides I, II, III, IV, soyasaponin I as well as quinones: kushequinone A. The part above ground contains alkaloids: matrine, oxymatrine, -allomatrine, isomatrine, sophoranol, sophoranol N-oxide, anagyrine, baptifoline, 1-N-methylcytisine, l-sophocarpine, l-sophoramine, d-N-oxysophocarpine, 1-Δ7-dehydrosophoramine, isosophocarpine, l-13,14-dehydrosophoridine, d-9a-hydroxymatrine, l-9a-hydroxysophocarpine, l-9a-hydroxysophocarpine N-oxide, l-7,8-dehydrosophoramine, l-9a-hydroxysophoramine, dimer of N-methylcytisine, sophoridine, d-12-dehydromatrine (lehmannine). The root also contains 2-alkylchromone derivatives, which are mainly 2-n-heneicosyl-5,7-dihydroxy-6,8-dimethyl chromone and 2-n-tricosyl-5,7-dihydroxy-6,8-dimethylchromone, and also 2-n-tridecyl-, 2-n-pentadecyl-, 2-n-heptadecyl-, 2-n-nonadecyl and 2-n-pentacosyl)-5,7-dihydroxyl-6,8-dimethylchromone.

In some embodiments, an extraction method of said *sophora flavescens* extract is: *sophora flavescens* is washed, chopped, then added into citric acid aqueous solution, immersed for 2-3 hours, then heated by microwave and extracted for 2-3 times and filtered, the filtrate is dried under a reduced pressure, to obtain the extract.

In some embodiments, the mass concentration of the said citric acid aqueous solution is 2-5 g/L.

In some embodiments, the weight ratio of said *sophora flavescens* to the citric acid aqueous solution was 1:(9-11).

In process of the experiment, the inventors found that the *sophora flavescens* extract obtained by extracting *sophora flavescens* with water may precipitate from the air scavenger composition being rested for a long time, and the effect will be affected, but this problem can be solved by immersing the *sophora flavescens* extract with citric acid aqueous solution and then heating with microwave during the extraction. The inventors deduced that the possible reason is that citric acid can promote dissolution of matrine from *sophora flavescens*, adjust pH value of the composition, making its stability higher.

Extract of *Robinia pseudoacacia*

*Robinia pseudoacacia* is leguminous plant *robinia pseudoacacia*, it is also called: acacia false, black locust. According to taxonomy, *robinia pseudoacacia* is also classified into *robinia pseudoacacia* 'Bessouiana', *robinia pseudoacacia* 'Frisia', *robinia pseudoacacia* 'Tortuosa', *robinia pseudoacacia* 'Pyramidalis', *robinia pseudoacacia* 'Umbraculifera', *robinia pseudoacacia* 'Stricta', *robinia pseudoacacia* 'Decaisneana', *robinia pseudoacacia* Var. inermisDC, *robinia pseudoacacia* Var. *microphylla*, *robinia pseudoacacia* 'upright', *robinia pseudoacacia* 'yellow', *R. pseudoacacia* f. umbraculifera, pink blossom *robinia pseudoacacia* and *robinia pseudoacacia* L.

In the present invention, *robinia pseudoacacia* 'Frisia' and *robinia pseudoacacia* 'Decaisneana' are chosen and blended in a weight ratio of 1:50 and extracted.

For said extract of *robinia pseudoacacia*, preferably leaves and flowers of *robinia pseudoacacia* were extracted.

In some embodiments, the extraction method of said *robinia pseudoacacia* extract is:

(1) Leaves of *robinia pseudoacacia* 'Frisia' and leaves of *robinia pseudoacacia* 'Decaisneana' are blended in a weight ratio of 1:50, washed, chopped, then wetted with ammonia water, added with ethanol, refluxed for 1-3 hours, and filtered while being hot, concentrated until no ethanol is present, to obtain the extract of leaves of *robinia pseudoacacia*.

(2) Flowers of *robinia pseudoacacia* 'Frisia' and flowers of *robinia pseudoacacia* 'Decaisneana' are blended in a weight ratio of 0.5:1.2, washed, chopped, added with honey, refluxed for 1-3 hours, and filtered while being hot, and concentrated until no ethanol is present, to obtain the extract of flowers of *robinia pseudoacacia*.

(3) the extract of leaves of *robinia pseudoacacia* and the extract of flowers of *robinia pseudoacacia* obtained in step 1 and step 2 are mixed, added into ethanol, ultrasonic agitated for 2.5 hours, concentrated until no ethanol is present, to obtain the extract of *robinia pseudoacacia*.

Extract of *Eucalyptus* Leaves

*Eucalyptus* is also called Youjialishu in Chinese, it is the general designation of plants of *Myrtaceae angophora, Corymbia* and *eucalyptus* L'Her., with origins in Indonesia and Australia etc. *eucalyptus* has multiple types, such as hard leaf arbor type in arid areas, hard leaf arbor type in moist areas, savanna type, arbor type in arid areas, high mountain meadow type. Species of said "*Eucalyptus*" that can be listed comprise: *eucalyptus globulus, eucalyptus maidenii, eucalyptus citriodora, eucalyptus robusta* Smith, leaf-type *E. cinerea, eucalyptus urophylla, eucalyptus grandis, eucalyptus tereticornis, eucalyptus globulus*, EuCahetus dunnii Maiden, *eucalyptus. saligna* Sm., *eucalyptus urophylla×E. grandis, eucalyptus grandis×E. urophylla, E. urophyllax E. camaldulensis, eucalyptus camaldulensis* Dehnh., EuCahetus dunnii Maiden, etc.

*Eucalyptus* leaves contain macrocarpals A, B, C, D, E, n-tritriacontane-16,18-dione, and the leaves and buds contain euglobal, the leaves also contain flavonoids: quercetol (i.e., quercetin), quercitrin, rutin, hyperoside, quercetol-3-glucoside, as well as gallic acid, caffeic acid, ferulic acid, gallic acid, protocate-chuic acid. Wax on the leaf surface contains 5,4-dihydroxy-7-methoxy-6-methylflavone, chrysin, eucalyptin, 8-demethyleu-calyptin, and 4,5-dihydroxyl-7-methoxyl-6,8-dimethylflavone (sideroxylin). Volatile oil in the leaves mainly contains cineole and also caryophyllene. Tritriacontane-16,18-dione, 3-O-methylellagic acid-4-rhamnoside, ellagic acid and el-lagitannin are isolated from the bark and xylem.

In some embodiments, the extraction method of said extract of *eucalyptus* leaves is: blended powders of barks of *eucalyptus robusta* Smith and leaves of *eucalyptus robusta* Smith are weighed in a weight ratio of 1:18, added into ethanol with a mass concentration of 80%, immersed for 3 hours, then heated by microwave, extracted 3 time, and filtered, the filtrate is concentrated under a reduced pressure until no ethanol is present, to obtain the extract.

Extract of *Chrysanthemum*

In the present invention, said "*chrysanthemum*" is a perennial root herbaceous plant of dendranthema of compositae, according to plant taxonomy. It is classified as spray *chrysanthemum*, single-stem *chrysanthemum*, Dali *chrysanthemum*, Xuanya *chrysanthemum*, Yi *chrysanthemum*, Antou *chrysanthemum*, etc. according to cultivation mode. *chrysanthemum* is cold in nature, bitter in taste, pungent, belongs to liver and heart channels.

Chemical components of *chrysanthemum* are: volatile oil components, flavone components, phenolic acid components and other components.

Components of the volatile oil are mainly monoterpenes, sesquiterpenes and its oxygen-containing deravatives and aliphatic compounds, etc., and volatile oil also contains *chrysanthemum* lactone, *chrysanthemum* alcohol, chrysantetriol, chrysanthenone, cis-spiroenol ether, trans-spiroenol ether, angeloylcumambrin B, angeloylajadin, Scotland artemisin A (arteglasin A), ambrosin A, ursolic acid, β-sitosterol, etc.

Main components of Flavones are: luteolin-7-O-β-glucopyranoside, buddleoside, luteolin, celereoin, acacetin-7-glucorhamnoside, luteolin-7-glucoside, quercitrin, apigenin-7-O-β-D-glucopyranoside, diosmetin-7-O-β-D-glucopyranosides, quercetin-3,7-di-O-β-D-glucopyranosides, eriodictyol-7-O-β-D-glucopyranoside, 1-phenyl-2,3-butanediol-3-O-β-D-glucopyranosides and hesperidin-7-O-β-D-glucurono-pyranoside.

The phenolic acid components comprise: 3-O-caffeoylquinic acid, 4-O-caffeoylquinic acid, 5-O-caffeoylquinic acid, 3,5-dicaffeoylquinic acid methyl ester, 3,5-dicaffeoylquinic acid, trans-3,5-dicaffeoyl quinic acid, 1,5-dicaffeoyl quinic acid, 1,3-dicaffeoyl quinic acid and chlorogenic acid, etc.

Other components comprise: besides volatile oil components, flavone components and phenolic acid components, various trace elements, such as Ca, Mg, Fe etc.; and proteins, amino acids, cholines, stachydrines, purines, tannins, vitamins, chlorophyls, carotenes, glyceryl behenate and palmitic acid, etc.

There are many extraction methods for *chrysanthemum*, such as: reflux extraction method, ultrasonic extraction method, steam distillation method, microwave extraction method, smashing tissue extraction method and supercritical $CO_2$ extraction method.

In a preferred embodiment, extraction method of said *chrysanthemum* extract is: 5 g of *chrysanthemum* is weighed, chopped, added into ethanol, immersed for 2-3 hours, heated by microwave and extracted for 2-3 times and filtered, the filtrate was concentrated under a reduced pressure until no ethanol is present, to obtain the extract.

Extract of *Aloe vera*

In the present invention, said "*aloe vera*" is a drought resistant liliaceae herbaceous plant, its scientific name is "*aloe vera*", distributes mainly in Africa and other places. *aloe vera* has antibacterial, anti-inflammatory and laxative efficacies, and thus is frequently used in treatment of heat in liver, flatulence, constipation, headache, tinea and calculus, etc. Fresh *aloe vera* has high contents of polysaccharides and anthraquinones, which are main active components. *aloe vera* gel contains a great amount of saccharide components, most of them are different types of glucomannan, in which acetylated mannan has a higher bioactivity. Other monosaccharides included are common arabinose, galactose, glucose, mannose and rhamnose, etc. Anthraquinone substances are mostly distributed in hypophloeodal palisade paranchyma, mainly are aloin and *aloe emodin*, which partly bind with polysaccharide to form glycoproteins, and partly exist as enzymes, such as hydroxy peptidase, peroxidase, cellulase and superoxide dismutase, etc. *aloe vera* also contains lactic acid, succinic acid, malic acid, p-coumaric acid, succinic acid and citric acid, etc.

In a preferred embodiment, extraction method of extract of said *aloe vera* is: 20 g of *aloe vera* is washed, then chopped, and uniformly mixed with a processed honey, then heated to 60° C., incubated for 3 hours, cooled, then water Is used as a solvent, ultrasonic extracted for 3-5 hours, extracted 3 times, the extracted solution are combined, filtered, then concentrated until no water is present, to obtain the extract.

The term "processed honey" refers to honey treated by the following process: honey is placed into a kettle, gently heated to boiling, then switched to a slow fire, keeping slight boiling, and removing foam and floating waxes, then removing dead bee and impurities by a sieve or filter cloth, and poured into the kettle, heated to 100° C.-118° C., when fisheye foams occur in the whole kettle, stickiness can be feeled when the honey is twiddled with hand, when long and white filament have not appeared between two fingers, the honey is quickly taken out of the kettle.

Nanosilver

Because nanosilver has a very large specific surface area, silver ions can be dissociated into an aqueous solution, sterilization mechanism of nanosilver is similar to that of silver ion, but effective concentration of nanosilver is totally different from that of silver ion. The smaller the particle diameter of nanosilver is, the higher permeability and bactericidal capability are. Size of the nanosilver particle is smaller, it can easily enter pathogen, and quickly bind with mercapto group of enzyme protein in bacteria, making some enzymes requiring mercapto group lose their activity, causing the pathogenic bacteria unable to metabolize and die, so as to achieve the effects of sterilization, tissue repair, and promoting wound healing. Nanosilver can bind with DNA base in the pathogenic bacteria and form a cross connection, and substitute hydrogen bonds between adjacent nitrogen atoms in purine and pyrimidine, causing loss of bacterial DNA replication capability and protein inactivation, and thus leading to inactivation of pathogenic bacteria. Nanosilver can also react with amino and carboxyl groups in bacteria, achieving an effect of killing bacteria or mould. Nanosilver is capable of killing *staphylococcus aureus, escherichia coli, pseudomonas aeruginosa, candida albicans, streptococcus pyogenes, enterococcus, chlamydia trachomatis, neisseria gonorrhoeae*, etc.

Nanosilver, as a new broad-spectrum bactericide, can kill various harmful bacteria in a short period of time, without inducing any resistance. It has a strong permeability, can deeply enter into the subcutaneous tissue from the pores of the skin, it has a good bactericidal effect on infections caused the common bacteria, stubborn bacteria, resistant bacteria and fungi. Nanosilver can also promote wound healing, improve the blood circulation of the tissue around the wound, and promote cell growth, accelerate wound healing, and reduce scar.

As a preferred solution of the present invention, particle diameter of said nanosilver is 1-20 nm, preferably 1-10 nm.

For preparation of nanosilver, physicochemical method and chemical reduction method can be adopted. The physicochemical method can be classified into photo quantum reduction method, laser stripping method, high-voltage magnetron sputtering method and ultrasonic method; the chemical reduction method comprises silver ammonia complex ion reduction method, electrochemical reduction method and reverse micelle method.

Photo quantum reduction method is an important method for the preparing nanosilver particles. Its basic principle is to produce hydrated electrons and reductive radical groups in solution by light irradiation. Hydrated electrons or radical groups can reduce silver ions in the solution to form activated silver, which can be continuously accumulated into larger particles and then make the particles stabilized by polymer or other medium. The method has good reproducibility in preparing nanosilver and is carried out at room temperature without interference by possibly introduced impurities. The reduction process of the photo quantum reduction method is homogeneous reaction. In addition, hydrated electrons or reductive radical groups can be produced by ultraviolet irradiation.

The preparation process of laser stripping method is as follow: a silver foil is placed on the bottom of a glass container, and 10 ml of solution of surfactant (such as sodium lauryl sulfate or sodium dodecylsulphate) is added, the solvent can be water, butanol, hexane, etc. A second harmonic radiation, with a wavelength of 532 nm, a pulse width of 10 ns, and a repetition frequency of 10 Hz is produced by a laser focusing len to irradiate the silver foil. Laser beam spot size is adjusted to 1-3 mm by adjusting the distance between the lens and the silver foil. After laser irradiation, plasma can be generated to convert the silver foil into nano particles. Then, the nano particles are collected by centrifugation and decantation.

High voltage magnetron sputtering method requires an inert gas (e.g., helium, argon, krypton) atmosphere, the gas pressure is maintained between 3 mtorr and 1 torr, the sputtering source may employ a DC power supply, with an axis length of about 200 mm, a plane diameter of about 50 mm, and a maximum output power of 1 kW. The sputtering voltage may be about 350V. When a stable plasma is formed, nanosilver particles obtained by the sputtering can be collected from a copper substrate cooled with liquid nitrogen. The distance between the substrate and the sample is about 5.5 cm.

Ultrasonic method uses ultrasonic wave generated by a ultrasonic generator to treat a $Ag^+$ solution containing surfactants (such as sodium dodecyl sulfate, sodium dodecyl benzene sulfonate, polyvinylpyrrolidone, polyoxyethylene sorbitan monolaurate, polyoxyethylene monostearate, etc.), nanoscale silver particles are obtained by reduction of $Ag^+$.

Silver ammonium complex ion reduction method produces nanoscale silver particles by adding concentrated ammonia water to a silver nitrate aqueous solution and then adding hydrogen peroxide dropwise, wherein the reaction is as follow:

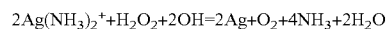

$$2Ag(NH_3)_2^+ + H_2O_2 + 2OH = 2Ag + O_2 + 4NH_3 + 2H_2O$$

The reaction is conducted at a low temperature, grain growth may not occur due to high temperature, and the size of silver particles are easy to control so that the size distribution of the product is narrow, and uniform. Another method is to add a stabilizer, such as polyvinylpyrrolidone, alkyl mercaptan, oleic acid and palmitic acid, etc., to silver ammonium complex ion in solution, and uses ascorbic acid or hydrate hydrazine or sodium borohydride to reduce the silver ammonium complex ions into nanosilver particles. Finally, the resultant nanosilver particles are immersed in a passivation agent, such as oleic acid, and the oleic acid is removed by filtration, then nanosilver particles is obtained by drying in vacuum. The nanosilver particles obtained by such preparation method have a good stability, and good dispersion.

The electrochemical reduction method prepares nanometal by electrode reaction, the method has a high yield, the products are easy to be separated, there are no metal hydride or boron impurities in the reaction process. The method can control the particle size by changing current density, and can produce silver particles of 2-7 nm. Because metal anode dissolves in aprotic solvent, the prepared nanosilver particles are pure.

Reverse micelle method prepares nanosilver by reducing silver ions through colloid chemistry. Reverse micelle refers to a micelle formed when the concentration of a surfactant dissolved in an organic solvent exceeds the critical micelle concentration, in which hydrophilic groups point inwards and hydrophobic groups point outwards. The reverse micelle kernel can solubilize water molecules to form a water core, silver ions are reduced in the water core to form nanoparticles. For example, in a reverse micelle, silver nitrate is reduced by pentahydroxy flavone to produce silver particles of 1-1.5 nm. Nanosilver particles can also be loaded onto $\alpha$-$Al_2O_3$, silver ions can be injected into a stainless steel appliances and then reduced, nanosilver can be loaded on surface of nano activated carbon, nanosilver particles can be loaded onto various fabrics such as nylon-11, nylon-66, and also nanosilver particles can be loaded onto polypropylene non-woven fabric, and cotton fabric.

Artemisinin

Said artemisinin is a colorless needle-like crystal extracted from the compound inflorescence plant *artemisia annua*. Its chemical name is (3R,5aS,6R,8aS,9R,12S,12aR)-octahydro-3,6,9-trimethyl-3, 12-bridged oxygen-12H-pyran [4,3-j]-1, 2-benzodithia-10(3H)-one. Its molecular formula is $C_{15}H_{22}O_5$, belonging to sesquiterpene lactone. Said artemisinin has a peroxy bond, a 6-lactone ring, and a 1,2,4-trioxane unit including peroxide, which is very rare in nature, seven chiral centers are included in the molecule, it is characterized by cis-linkage of A ring and B ring, and isopropyl group and bridgehead hydrogen are of a trans relationship. Said artemisinin is easily soluble in chloroform, acetone, ethyl acetate and benzene, soluble in ethanol, ether, slightly soluble in cold petroleum ether, and almost insoluble in water. Because it has a special peroxy group, it is unstable to heat, and is easy to decompose under effect of moisture, heat and reductive substance. In the present invention, said artemisinin is purchased from Shanxi Senlang Biological Chemical Co. Ltd.

A second aspect of the present invention provides an air scavenger, comprising above-mentioned air scavenger composition.

Specific form of said air scavenger is not specifically limited, such as: paste, liquid, foam, spray, etc.

The air scavenger composition provided by the present invention can significantly improve purification effect on air by adding the extracts of *sanguisorba officinalis* and *melia azadarach*, and improve the stability of said air scavenger composition by adopting specific extraction method for the extract of *sophora flavescens*.

EXAMPLES

A1 Extracts of *Sanguisorba officinalis* and *Melia azadarach*

Extraction method: *sanguisorba officinalis* and *melia azadarach* are respectively washed, chopped, then *sanguisorba officinalis* and *melia azadarach* are uniformly mixed, extracted under reflux with ethanol for 3 hours, extracted 4 times, refrigerated for 12 hours, and filtered, the filtrate is concentrated under a reduced pressure until no ethanol is present, to obtain the extract.

The weight ratio of said *sanguisorba officinalis* to said *melia azadarach* is 1:3.

A2 Extracts of *Sanguisorba officinalis* and *Melia azadarach*

Extraction method: *sanguisorba officinalis* and *melia azadarach* are respectively washed, chopped, then *sanguisorba officinalis* and *melia azadarach* are uniformly mixed, extracted under reflux with water for 3 hours, extracted 4 times, refrigerated for 12 hours, and filtered, the filtrate is dried under a reduced pressure, to obtain the extract.

The weight ratio of said *sanguisorba officinalis* to said *melia azadarach* is 1:3.

A3 Extracts of *Sanguisorba officinalis* and *Melia azadarach*

Extraction method: *sanguisorba officinalis* is washed, chopped, then extracted under reflux with ethanol for 3 hours, extracted 4 times, and refrigerated for 12 hours, and filtered the filtrate is concentrated under a reduced pressure until no ethanol is-present, to obtain the extract of *sanguisorba officinalis*; *melia azadarach* is washed, chopped, then extracted under reflux with ethanol for 3 hours, extracted 4 times, refrigerated for 12 hours, and filtered, the filtrate is concentrated under a reduced pressure until no ethanol is present, to obtain the extract of *melia azadarach*; the extract of *sanguisorba officinalis* and the extract of *melia azadarach* are uniformly mixed, to obtain the extract.

The weight ratio of said *sanguisorba officinalis* to said *melia azadarach* is 1:3.

B1 Extract of *Sophora flavescens*

Extraction method: *sophora flavescens* is washed, chopped, then added into a citric acid aqueous solution, immersed for 3 hours, then heated by microwave and extracted for 3 times and filtered, the filtrate is dried under a reduced pressure, to obtain the extract.

The mass concentration of said citric acid aqueous solution is 4 g/L.

The weight ratio of said *sophora flavescens* to the citric acid aqueous solution is 1:10.

B2 Extract of *Sophora flavescens*

Extraction method: *sophora flavescens* is washed, chopped, then added into an aqueous solution, immersed for 3 hours, then heated by microwave and extracted 3 times and filtered, the filtrate is dried under a reduced pressure, to obtain the extract.

The mass concentration of said citric acid aqueous solution is 4 g/L.

The weight ratio of said *sophora flavescens* to the citric acid aqueous solution is 1:10.

C Extract of *Robinia pseudoacacia*

Extraction Method:

(1) Leaves of *robinia pseudoacacia* 'Frisia' and leaves of *robinia pseudoacacia* 'Decaisneana' are blended in a weight ratio of 1:50, washed, chopped, then wetted with ammonia water, added with ethanol, refluxed for 2 hours, and filtered while being hot, concentrated until no ethanol is present, to obtain the extract of leaves of *robinia pseudoacacia*.

(2) Flowers of *robinia pseudoacacia* 'Frisia' and flowers of *robinia pseudoacacia* 'Decaisneana' are blended in a weight ratio of 0.5:1.2, washed, chopped, added with honey, refluxed for 2 hours, and filtered while being hot, and concentrated until no ethanol is present, to obtain the extract of flowers of *robinia pseudoacacia*.

(3) the extract of leaves of *robinia pseudoacacia* and the extract of flowers of *robinia pseudoacacia* obtained in step 1 and step 2 are mixed, added into ethanol, ultrasonic agitated for 2.5 hours, concentrated until no ethanol is present, to obtain the extract of *robinia pseudoacacia*.

D Extract of *Eucalyptus* Leaves

Extraction method: a blended powder of barks of *eucalyptus robusta* Smith and leaves of *eucalyptus robusta* Smith is weighed in a weight ratio of 1:18, added into ethanol with a mass concentration of 80%, immersed for 3 hours, then heated by microwave and extracted 3 times and filtered, the filtrate is concentrated under a reduced pressure until no ethanol is present, to obtain the extract.

E Extract of *Chrysanthemum*

Extraction method: 5 g of *chrysanthemum* is weighed, chopped, added into ethanol, and immersed for 2 hours and heated by microwave and extracted 3 times and filtered, the filtrate is concentrated under a reduced pressure until no ethanol is present, to obtain the extract.

F Extract of *Aloe vera*

Extraction method: 20 g of *aloe vera* is washed, chopped, and uniformly mixed with processed honey, then heated to 60° C., incubated for 3 hours, cooled, then water is used as solvent, extracted by ultrasonic wave for 3 hours, extracted 3 times, the extracted liquids are combined, filtered, and then concentrated until no water is present, to obtain the extract.

G Nanosilver
Particle diameter is 5 nm, Jida Tech JDTKS-001.
H Artemisinin
Shaanxi Senlang Biological Chemical Co. Ltd.
The weight parts of the raw materials of Examples 1-5 and Comparative Example 1-5 are listed in Table 1.

TABLE 1

|  | A1 | A2 | A3 | B1 | B2 | C | D | E | F | G | H |
|---|---|---|---|---|---|---|---|---|---|---|---|
| Example 1 | 20 |  |  | 20 |  | 8 | 3 | 13 | 12 | 0.5 | 1 |
| Example 2 | 15 |  |  | 25 |  | 7 | 2 | 12 | 11 | 0.4 | 0.8 |
| Example 3 | 25 |  |  | 15 |  | 8 | 4 | 14 | 13 | 0.6 | 1.2 |
| Example 4 | 10 |  |  | 30 |  | 5 | 1 | 10 | 10 | 1 | 2 |
| Example 5 | 30 |  |  | 10 |  | 10 | 5 | 15 | 15 | 0.1 | 0.5 |
| Comparative Example 1 |  | 20 |  | 20 |  | 8 | 3 | 13 | 12 | 0.5 | 1 |
| Comparative Example 2 |  |  | 20 | 20 |  | 8 | 3 | 13 | 12 | 0.5 | 1 |
| Comparative Example 3 | 20 |  |  |  | 20 | 8 | 3 | 13 | 12 | 0.5 | 1 |
| Comparative Example 4 |  |  |  | 20 |  | 8 | 3 | 13 | 12 | 0.5 | 1 |
| Comparative Example 5 | 20 |  |  |  |  | 8 | 3 | 13 | 12 | 0.5 | 1 |

Test Method

Air scavenger contents in Example 1 or Comparative Example 1-5 are 10 wt %, content of 1,2-propanediol is 20 wt %, content of palmitic acid is 15 wt %, content of stearic acid is 6 wt %, content of sodium hydroxide is 3 wt %, content of vitamin E acetate is 0.1 wt %, the remaining is water.

Preparation of the air scavenger: 1,2-propanediol, palmitic acid, stearic acid, sodium hydroxide, Vitamin E acetate, water and the mixture in Example 1 or Comparative Examples 1-5 are mixed according to the above-mentioned ratios at 45° C., stirred for 4 hours, evaporated to dryness, to obtain a paste air scavenger.

The air scavenger prepared according to the above-mentioned method is tested.

1. Effective Duration Experiment:

1.1 Fresh Air Scavenger

A certain volume of chemical pure formaldehyde (or benzene or ammonia) is injected into a 1 m³ sealed laboratory chamber, a fan in the chamber is started, immediately after 1 hour the concentration of gas in the test chamber is tested as an initial concentration. In the 1 m³ sealed laboratory chamber, the prepared air scavenger is put into the chamber. Immediately after 72 hours, the gas concentration in the chamber is sampled and tested, and a removal rate is calculated according to the removal rate=(initial concentration−sample concentration)×100/initial concentration. The test results are shown in Table 2.

1.2 the Air Scavenger is Shelved for Two Months

Specific experiment step is the same as 1.1 except for that the air scavenger is shelved for two months, then it is subjected to the same test, the test results are shown in Table 2.

Wherein, TVOC is total volatile organic compounds, all indoor organic gaseous substances.

1.3 Stability Test

The air scavenger is rested in a sealed transparent container for 12 months, the time required by precipitation emergence is recorded. No precipitating is denoted by A, precipitating at 9-11 months is denoted by B, precipitating at 3-8 months is denoted by C, precipitating at 1-2 month is recorded as D, precipitating within 1 months is recorded as E, the test results are shown in Table 2.

TABLE 2

|  |  | removal rate of formaldehyde (%) | removal rate of benzene (%) | removal rate of ammonia (%) | removal rate of TVOC (%) | stability test |
|---|---|---|---|---|---|---|
| Example 1 | fresh | 98.2 | 97.4 | 99.6 | 99.3 | A |
|  | shelved for 2 months | 96.4 | 95.5 | 98.2 | 97.2 |  |
| Comparative Example 1 | fresh | 84.2 | 83.9 | 84.1 | 78.5 | A |
|  | shelved for 2 months | 72.1 | 71.2 | 68.5 | 66.4 |  |
| Comparative Example 2 | fresh | 79.3 | 83.1 | 78.6 | 71.3 | A |
|  | shelved for 2 months | 71.2 | 74.2 | 68.6 | 60.8 |  |
| Comparative Example 3 | fresh | 92.9 | 91.1 | 75.2 | 72.5 | E |
|  | shelved for 2 months | 36.8 | 34.4 | 30.1 | 29.7 |  |
| Comparative Example 4 | fresh | 60.2 | 68.1 | 67.3 | 64.6 | A |
|  | shelved for 2 months | 51.2 | 55.3 | 54.2 | 51.8 |  |
| Comparative Example 5 | fresh | 76.7 | 79.2 | 72.1 | 68.3 | E |
|  | shelved for 2 months | 25.2 | 29.8 | 34.4 | 20.2 |  |

As seen from Table 2, by using the air scavenger composition provided by the present invention, and by adding extracts of *sanguisorba officinalis* and *melia azadarach*, purifying effect on air can be significantly improved, meanwhile a specific extraction method is adopted for *sophora flavescens* extract, resulting in that said air scavenger composition has a higher stability.

The invention claimed is:

1. An air scavenger composition, comprising by weight:

| extracts of *sanguisorba officinalis* and *melia azedarach* | 10-30 parts; |
|---|---|
| extract of *sophora flavescens* | 10-30 parts; |
| extract of *robinia pseudoacacia* | 5-10 parts; |
| extract of *eucalyptus* leaves | 1-5 parts; |
| extract of *chrysanthemum* | 10-15 parts; |
| extract of *aloe vera* | 10-15 parts; |
| nanosilver | 0.1-1 part; and |
| artemisinin | 0.5-2 parts. | wherein said *sophora flavescens* extract is obtained by washing, chopping, and then adding the *sophora flavescens* into a citric acid aqueous solution, immersing for 3 hours, then heating by microwave and extracting for 3 times and filtering, the filtrate is then dried under a reduced pressure; to obtain the extract; wherein the mass concentration of said citric acid aqueous solution is 4 g/L; and the weight ratio of said *sophora flavescens* to the citric acid aqueous solution is 1:10; and wherein said *sanguisorba officinalis* and *melia azedarcha* extracts are obtained by separately washing and chopping each of said *sanguisorba officinalis* and *melia azadarach*, then uniformly mixing the washed, chopped *sanguisorba officinalis* and *melia azedarcha*, extracting under reflux with ethanol for 2-3 hours 3-4 times, refrigerating for 10-15 hours, and filtering, the filtrate is then concentrated under a reduced pressure until no ethanol is present to obtain the extracts; wherein the weight ratio of said *sanguisorba officinalis* to said *melia azadarach* is 1:(2.5-3.5).

2. The air scavenger composition according to claim 1, comprising by weight:

| | |
|---|---|
| extracts of *sanguisorba officinalis* and *melia azedarach* | 15-25 parts; |
| extract of *sophora flavescens* | 15-25 parts; |
| extract of *robinia pseudoacacia* | 7-8 parts; |
| extract of *eucalyptus* leaves | 2-4 parts; |
| extract of *chrysanthemum* | 12-14 parts; |
| extract of *aloe vera* | 11-13 parts; |
| nanosilver | 0.4-0.6 part; and |
| Artemisinin | 0.8-1.2 parts. |

3. The air scavenger composition according to claim 1, comprising by weight:

| | |
|---|---|
| extracts of *sanguisorba officinalis* and *melia azedarach* | 20 parts; |
| extract of *sophora flavescens* | 20 parts; |
| extract of *robinia pseudoacacia* | 8 parts; |
| extract of *eucalyptus* leaves | 3 parts; |
| extract of *chrysanthemum* | 13 parts; |
| extract of *aloe vera* | 12 parts; |
| nanosilver | 0.5 parts; and |
| Artemisinin | 1 part. |

4. The air scavenger composition according to claim 1, wherein particle diameter of said nanosilver is 1-20 nm.

5. An air scavenger paste, liquid, foam, or spray, including said air scavenger composition according to claim 1.

6. An air scavenger paste, liquid, foam, or spray, including said air scavenger composition according to claim 2.

7. An air scavenger paste, liquid, foam, or spray, including said air scavenger composition according to claim 3.

8. An air scavenger paste, liquid, foam, or spray, including said air scavenger composition according to claim 4.

* * * * *